United States Patent
Chah et al.

(10) Patent No.: US 11,998,485 B2
(45) Date of Patent: Jun. 4, 2024

(54) OPHTHALMIC SURGICAL APPARATUS

(71) Applicant: CHOI'S OPHTHALMIC INSTITUTE, Seoul (KR)

(72) Inventors: Hung Won Chah, Seoul (KR); Soon Ki Lim, Seoul (KR); Woon Jung Cho, Seoul (KR)

(73) Assignee: CHOI'S OPHTHALMIC INSTITUTE, Seoul (KR)

( * ) Notice: Subject to any disclaimer, the term of this patent is extended or adjusted under 35 U.S.C. 154(b) by 894 days.

(21) Appl. No.: 16/964,707

(22) PCT Filed: Nov. 28, 2018

(86) PCT No.: PCT/KR2018/014801
§ 371 (c)(1),
(2) Date: Jul. 24, 2020

(87) PCT Pub. No.: WO2019/177227
PCT Pub. Date: Sep. 19, 2019

(65) Prior Publication Data
US 2020/0345547 A1 Nov. 5, 2020

(30) Foreign Application Priority Data
Mar. 12, 2018 (KR) ........................ 10-2018-0028845

(51) Int. Cl.
*A61B 18/14* (2006.01)
*A61F 9/007* (2006.01)
*A61B 18/00* (2006.01)

(52) U.S. Cl.
CPC .. *A61F 9/0079* (2013.01); *A61B 2018/00077* (2013.01); *A61B 2018/00321* (2013.01);
(Continued)

(58) Field of Classification Search
CPC ............... A61F 9/0079; A61B 18/1477; A61B 2018/00964; A61B 2018/1495; A61B 2018/144
See application file for complete search history.

(56) References Cited

U.S. PATENT DOCUMENTS

| 4,985,035 A | 1/1991 | Torre |
| 5,755,716 A | 5/1998 | Garito et al. |
(Continued)

FOREIGN PATENT DOCUMENTS

| JP | 2001-517974 A | 10/2001 |
| KR | 10-1999-0077048 A | 10/1999 |
(Continued)

OTHER PUBLICATIONS

International Search Report and Written Opinion for PCT/KR2018/014801 dated Mar. 4, 2019, all pages.
(Continued)

*Primary Examiner* — Jaymi E Della
(74) *Attorney, Agent, or Firm* — Kilpatrick Townsend & Stockton LLP

(57) ABSTRACT

An ophthalmic surgical apparatus includes: a support provided with an electrical path, and a probe including a conductive material, the probe including a first section coupled to the support and a second section formed integrally with and connected to the first section, the entire surface of the second section being exposed to the outside of the support.

14 Claims, 5 Drawing Sheets

(52) U.S. Cl.
CPC . *A61B 2018/00964* (2013.01); *A61B 18/1477* (2013.01); *A61B 2018/1495* (2013.01)

(56) References Cited

U.S. PATENT DOCUMENTS

| | | | |
|---|---|---|---|
| 5,814,043 A * | 9/1998 | Shapeton | A61B 18/1402 606/41 |
| 2002/0049437 A1 * | 4/2002 | Silvestrini | A61F 9/013 606/49 |
| 2002/0126501 A1 | 9/2002 | Toth et al. | |
| 2007/0027443 A1 | 2/2007 | Rose et al. | |
| 2008/0119842 A1 * | 5/2008 | Palanker | A61B 17/30 606/205 |
| 2011/0288543 A1 | 11/2011 | Cheng et al. | |

FOREIGN PATENT DOCUMENTS

| | | | | |
|---|---|---|---|---|
| KR | 10-2008-0092400 A | 10/2008 | | |
| KR | 10-1812480 B1 | 1/2018 | | |
| WO | 2009/073619 A2 | 6/2009 | | |
| WO | 2016/022789 A1 | 2/2016 | | |
| WO | WO-2016022789 A1 * | 2/2016 | ......... | A61B 18/1402 |
| WO | 2019/177227 A1 | 9/2019 | | |

OTHER PUBLICATIONS

Supplementary European Search Report for EP 18910109 dated Oct. 14, 2021, 6 pages.
Office Action dated Nov. 11, 2021 for CN 201880087902, 8 pages.
Notification of Reasons for Refusal for JP 2020-534153 dated Jan. 5, 2022, all pages.

\* cited by examiner

OPHTHALMIC SURGICAL APPARATUS

TECHNICAL FIELD

The present disclosure relates to an ophthalmic surgical apparatus, and more particularly, to an ophthalmic surgical apparatus capable of securing a field of view during surgery.

BACKGROUND ART

Electrosurgical instruments are generally well known and widely used in the medical, dental, and veterinary fields. In the course of surgery, a surgeon may perform a cutting procedure and a procedure for coagulating blood vessels by using electrosurgical instruments. Electrosurgical instruments provide setting of various operating parameters for a surgical procedure, such as power setting, temperature control, electrode configuration, and radiowave-frequency (RF) energy setting.

In a conventional electrosurgical instrument using RF energy, an insulating material such as Teflon that blocks the flow of electricity from a probe is coated. However, the probe becomes thicker due to the insulating material, and in particular, in the case of ophthalmic surgery using a surgical instrument in a vertical direction in a relatively narrow space, the field of view may be obscured by a thick probe or a user's finger.

In addition, the thickness of a conventional probe is 120 $\mu$m, which is significantly larger than the thickness of the conjunctiva, causing resistance in the process of piercing the conjunctiva, and there is a problem in that blood vessels and the like are undesirably damaged due to the resistance.

In addition, there is a problem in that an insulating material such as Teflon remains in the internal tissue under the conjunctiva, causing inflammation and the like.

DESCRIPTION OF EMBODIMENTS

Technical Problem

Provided is an ophthalmic surgical apparatus in which a certain section of a probe is exposed to the outside of a support and thus an insulating material is not required and the thickness of the probe is reduced and thus a field of view of a user may be secured during ophthalmic surgery.

However, this objective is exemplary, and the scope of the present disclosure is not limited thereby.

Solution to Problem

According to an aspect of the present disclosure, an ophthalmic surgical apparatus includes: a support provided with an electrical path, and a probe including a conductive material, the probe including a first section coupled to the support and a second section formed integrally with the first section and connected to the first section, the entire surface of the second section being exposed to the outside of the support.

The ratio of the diameter of the probe to the maximum length of the second section of the probe, which satisfies a certain surgical stability, may be 0.01 or more and 0.015 or less.

The ratio of the diameter of the probe to the length of the second section of the probe may be 0.0116 or more and 0.035 or less.

The ratio of the diameter of the probe to the diameter of the support may be 0.03 or more and 0.07 or less.

The diameter of the probe may be 30 $\mu$m or more and 70 $\mu$m or less.

The probe may have a linear shape.

The probe may have at least one bent portion formed in a longitudinal direction.

The support may have a cylindrical shape.

The first section of the probe may be concentric with the support and may be inserted into the support.

The ophthalmic surgical apparatus may further include: a holder into which the support is inserted, and a handpiece body coupled to the holder.

The diameter of the holder may be reduced further away from the handpiece body.

A longitudinal axis of the handpiece body and a longitudinal axis of the holder may be arranged to form a certain angle.

The holder may include: a holder body having an insertion portion formed to insert the support into the insertion portion, a button portion arranged on the other side opposite to one side of the holder body in which the insertion portion is formed, and an elastic support arranged between the button portion and the support inserted into the inside of the holder body.

The elastic support may include a coil-shaped spring.

The button portion may penetrate the holder body and may be reciprocally moved inside the holder body.

The holder may include: a holder body having an insertion portion formed to insert the support into the insertion portion, a button portion penetratingly coupled to the holder body, a moving portion that is in contact with the button portion and is movable on the insertion portion, and an elastic support arranged between the holder body and the moving portion, the elastic support elastically supporting the moving portion toward the holder body.

Other aspects, features, and advantages other than those described above will be apparent from the following drawings, claims, and detailed description of the present disclosure.

Advantageous Effects of Disclosure

According to an embodiment of the present disclosure made as described above, because the entire surface of a second section of a probe is exposed to the outside of a support, no separate insulating portion is required, and during ophthalmic surgery, a user's field of view may be prevented from being obstructed due to the thickness of the insulating portion.

In addition, because the ratio of the diameter of the second section of the probe to the length of the second section of the probe is 0.116 or more and 0.0175 or less, the rigidity of the probe may be secured, and by reducing the thickness of the probe, a user's field of view may be secured during ophthalmic surgery.

In addition, because the ratio of the diameter of the probe to the diameter of the support is 0.03 or more and 0.07 or less, the probe may be prevented from being obscured by the support during ophthalmic surgery and a user's field of view may be secured.

In addition, due to a button portion, when the use of the probe coupled to the support is completed, the support and the probe coupled to the support may be quickly removed from a holder body.

BEST MODE

Figure 1:
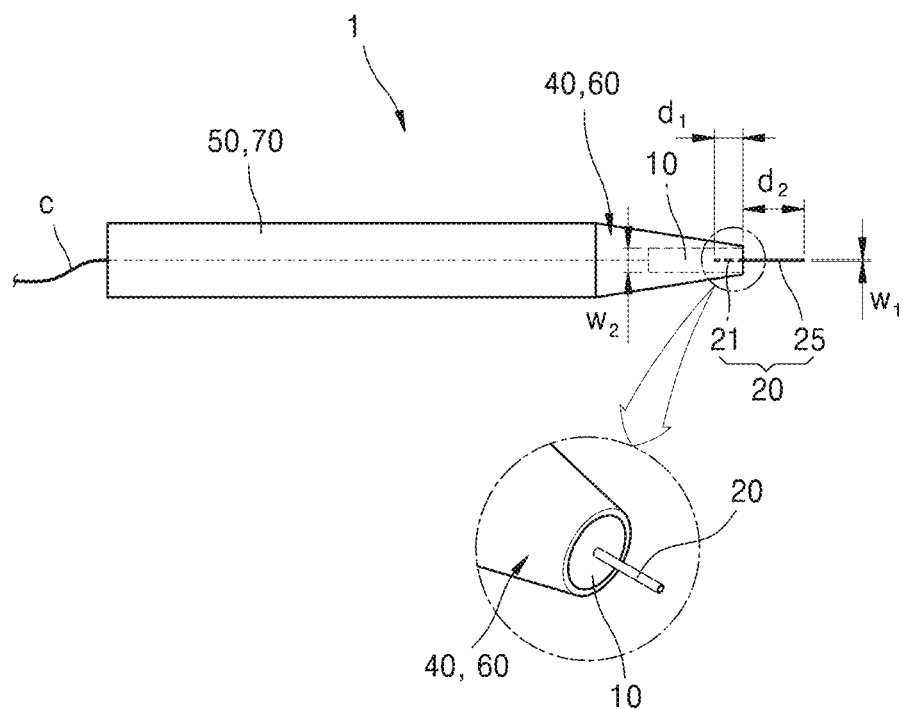
FIG. 1 is a side view illustrating an ophthalmic surgical apparatus according to an embodiment of the present disclosure.

As the present disclosure allows for various changes and numerous embodiments, particular embodiments will be illustrated in the drawings and described in detail, in the written description. Effects and features of the present disclosure and methods for achieving them will be clarified with reference to embodiments described below in detail with reference to the drawings. However, the present disclosure is not limited to the embodiments disclosed below and may be implemented in various forms.

Reference will now be made in detail to embodiments, examples of which are illustrated in the accompanying drawings, and the same elements in the drawings are denoted by the same reference numerals and a repeated explanation thereof will not be given.

It will be understood that although the terms "first", "second", etc. may be used herein to describe various components, these components should not be limited by these terms, are only used to distinguish one component from another.

As used herein, the singular forms "a", "an", and "the" are intended to include the plural forms as well, unless the context clearly indicates otherwise.

It will be further understood that the terms "comprises", "includes", "has", "comprising", "including", and/or "having" used herein specify the presence of stated features or components, but do not preclude the presence or addition of one or more other features or components.

Sizes of components in the drawings may be exaggerated for convenience of explanation. For example, because sizes and shapes of components in the drawings are arbitrarily illustrated for convenience of explanation, the present disclosure is not limited thereto.

Figure 2:
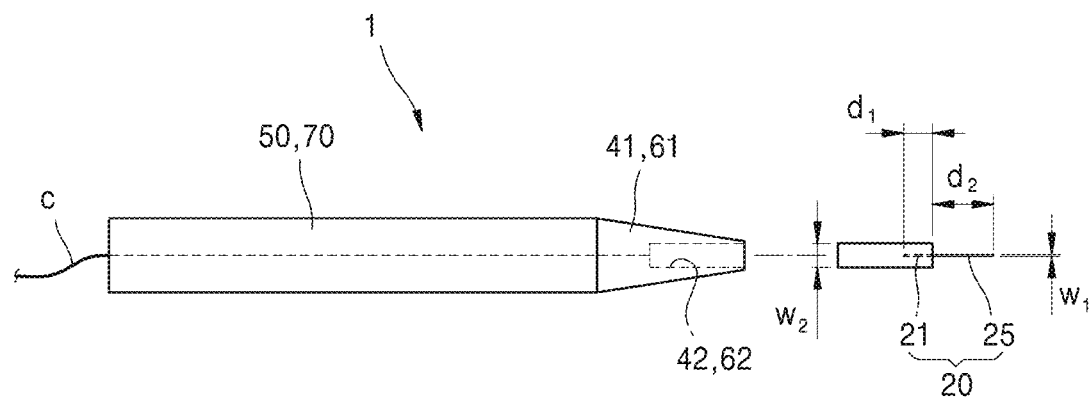
FIG. 2 is a side view illustrating an ophthalmic surgical apparatus from which a probe is separated.
Figure 3:
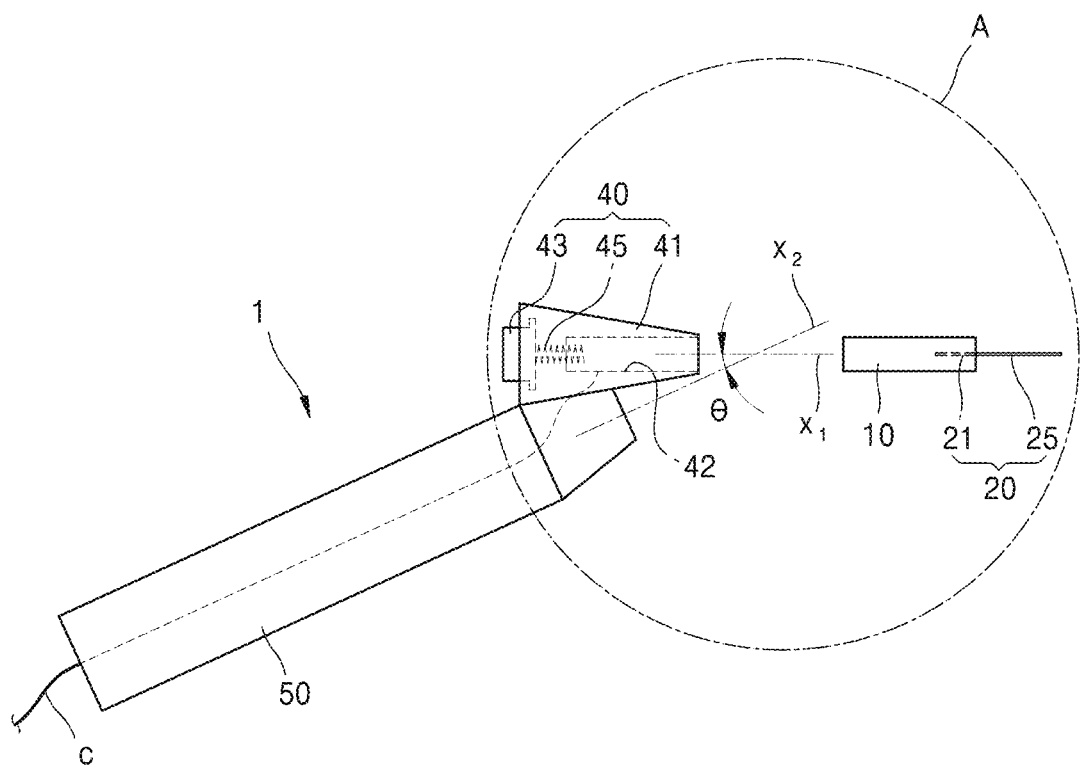
FIG. 3 is a side view illustrating an ophthalmic surgical apparatus according to an embodiment of the present disclosure.
Figure 4:
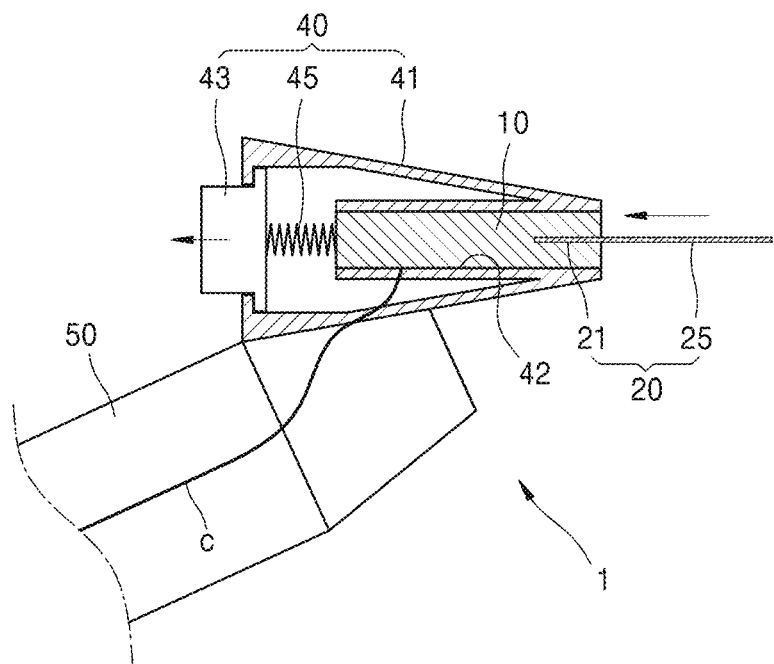
FIG. 4 is an enlarged view of portion A in FIG. 3.
Figure 5:
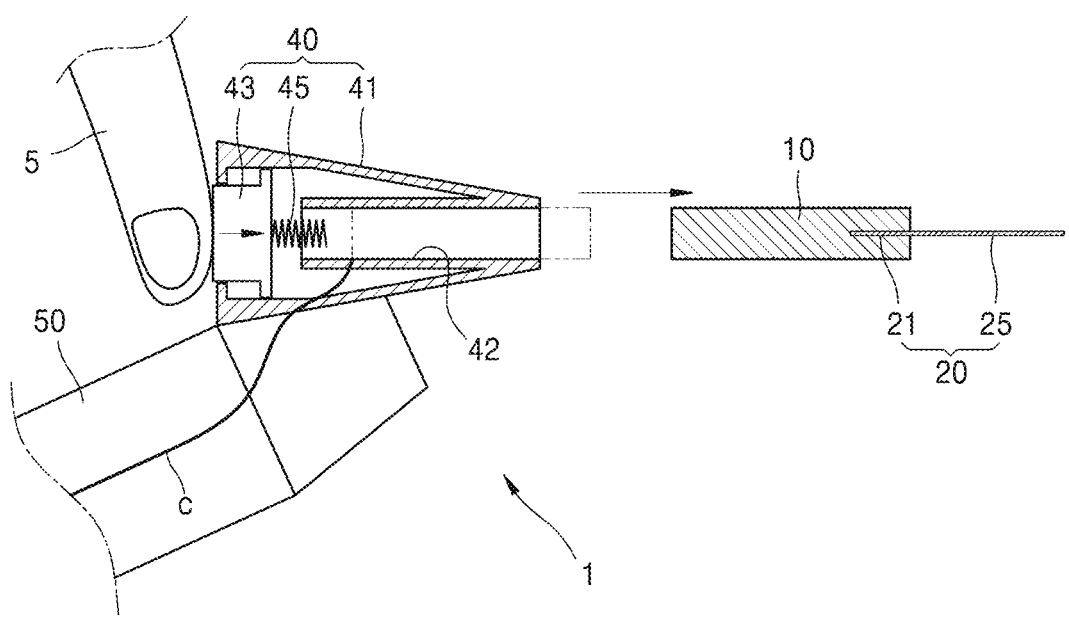
FIG. 5 is a side view illustrating a state in which a probe is removed from FIG. 3.

Hereinafter, ophthalmic surgical apparatuses according to embodiments of the present disclosure will be described in detail with reference to the drawings. FIG. 1 is a side view illustrating an ophthalmic surgical apparatus according to an embodiment of the present disclosure. FIG. 2 is a side view illustrating an ophthalmic surgical apparatus from which a probe is separated. FIG. 3 is a side view illustrating an ophthalmic surgical apparatus according to an embodiment of the present disclosure. FIG. 4 is an enlarged view of a portion A in FIG. 3. FIG. 5 is a side view illustrating a state in which a probe is removed from FIG. 3.

Referring to FIGS. 1 to 5, an ophthalmic surgical apparatus 1 according to an embodiment of the present disclosure may include a support 10, a probe 20, a holder 40, and a handpiece body 50.

The support 10 may be provided with an electrical path and may be formed of a conductive material. The handpiece body 50, which will be described later, may be connected to an electric wire C and the like to provide an electrical path, and may be supplied with power from the outside because the support 10 is coupled to the handpiece body 50.

Specifically, the support 10 may transmit an electrical signal such as a radio frequency (RF) signal to the probe 20 and contact an object, such as the conjunctiva, through the probe 20 to treat diseases such as conjunctivitis.

The support 10 may be formed in a cylindrical shape. The support 10 is formed in a cylindrical shape and is inserted into the holder 40 to be described later, specifically, an insertion portion 42 formed in a holder body 41. The holder body 41 may be provided with an insertion portion 42 having a hollow interior to correspond to the shape of the support 10. However, the spirit of the present disclosure is not limited thereto, and the support 10 may be formed in various shapes according to functions and shapes required for the ophthalmic surgical apparatus 1.

Referring to FIGS. 1 and 2, the probe 20 according to an embodiment of the present disclosure may be formed of a conductive material, and may directly contact a surgical site such as the conjunctiva. In an embodiment of the present disclosure, the probe 20 is formed to have the same diameter over the entire section to form a cylindrical shape, but various modifications may be made. For example, the diameter of the probe 20 may vary according to a certain section.

Referring to FIGS. 1 and 2, the probe 20 includes a first section 21 and a second section 25. The first section 21 is coupled to the support 10, that is, is inserted into the inside of the support 10 and coupled to the support 10. The first section 21 is arranged on one side of the probe 20, which is coupled to the support 10, and thus, the first section 21 is not exposed to the outside of the support 10. The first section 21 of the probe 20 may be integrally formed with the support 10 or may be formed as a separate member.

The first section 21, the second section 25, and the support 10 may be formed of a conductive material and may be supplied with an electrical signal such as an RF signal by providing an electrical path, and the probe 20 may contact a treatment target portion, such as the conjunctiva, thereby removing a damaged portion.

Referring to FIGS. 1 and 2, the second section 25 according to an embodiment of the present disclosure is integrally formed with and connected to the first section 21, and the entire surface of the second section 25 is exposed outside the support 10. Specifically, the second section 25 protrudes to the outside of the support 10 in a direction away from the handpiece body 50 to be described later, and the entire surface of the second section 25 is exposed to the outside.

In other words, in the integrally formed probe 20, a portion inserted into the support 10 may be defined as the first section 21 and a portion protruding outside the support 10 may be defined as the second section 25.

Because the second section 25 is formed of a conductive material, the fact that the front surface of the second section 25 is exposed to the outside means that a separate insulating portion is not formed along the outer circumferential surface of the second section 25.

Because a separate insulating portion is not formed along the outer circumferential surface of the second section 25, the thickness of the probe 20, specifically, the thickness of the second section 25 is not increased as much as the insulating portion. Therefore, there is an effect that a user may secure a field of view when performing surgery using the ophthalmic surgical apparatus 1.

The other end opposite to one end of the second section 25 connected to the first section 21 has a certain angle, and when viewed from the side, the cross section of the other end may have a triangular shape having a hypotenuse.

The angle between the hypotenuse and the longitudinal axis of the second section 25 may be 10 degrees. Due to this, compared to a case where the end of the second section 25, which is opposite to one side of the first section 21, is formed at about 30 degrees to about 45 degrees, a cross-sectional area in a certain section may be reduced, and thus, penetrability to objects such as the conjunctiva may be improved.

In addition, damage to an object due to the probe 20 may be prevented due to a reduction in the area of penetration to the object, such as the conjunctiva.

Table 1 below is a table showing the relationship between a diameter w1 of the probe 20 and a length d2 of the second section 25.

TABLE 1

|        | 2 mm | 3 mm | 4 mm | 5 mm | 6 mm | 7 mm |
|--------|------|------|------|------|------|------|
| 30 μm  | 2.5  | 2.5  | 1.25 | 1.25 | 1    | 1    |
| 45 μm  | 2.75 | 2.75 | 1.25 | 1.5  | 1.25 | 1.25 |
| 50 μm  | 3    | 3    | 2.5  | 2.25 | 2    | 1.25 |
| 70 μm  | 3    | 3    | 3    | 2.75 | 2.5  | 2    |

Referring to Table 1, a vertical item indicates the diameter w1 of the probe 20, and a horizontal item indicates the length d2 of the second section 25 of the probe 20. Table 1 shows a numerical value of surgical stability for the diameter w1 of the probe 20, and the surgical stability may be measured while varying the diameter w1 of the probe 20.

In this specification, the surgical stability may be determined in consideration of the degree of deformation according to the ratio of the diameter w1 of the probe 20 to the length d2 of the second section 25 and the degree of damage to an object, such as the conjunctiva, according to the diameter w1 of the probe 20. In general, when the value of the surgical stability is 2.5 or more, it is defined that a certain surgical stability is satisfied.

Referring to Table 1, the diameter w1 of the probe 20 according to an embodiment of the present disclosure may be formed to be 70 μm. When the diameter w1 of the probe 20 is 70 μm, the surgical stability satisfies a certain standard when the length d2 of the second section 25 is 6 mm or less.

Referring to Table 1, when surgical stability is measured while varying the diameter w1 of the probe 20, the length d2 of the second section 25, which satisfies a certain surgical stability, is 4 mm or less when the diameter w1 of the probe 20 is 50 μm, 3 mm or less when the diameter w1 of the probe 20 is 45 μm, and 3 mm or less when the diameter w1 of the probe 20 is 30 μm.

Therefore, the ratio of the diameter w1 of the probe 20 to the length d2 of the second section 25 of the probe 20, which satisfies a certain surgical stability, is 0.0116 when the diameter w1 of the probe 20 is 70 μm, 0.0125 when the diameter w1 of the probe 20 is 50 μm, 0.015 when the diameter w1 of the probe 20 is 45 μm, and 0.01 when the diameter w1 of the probe 20 is 30 μm.

In other words, when the ratio of the diameter w1 of the probe 20 to the length d2 of the second section 25 of the probe 20, which satisfies a certain surgical stability, is 0.01 or more and 0.015 or less, the probe 20 may satisfy a certain surgical stability.

Although not shown in the table, when the length d2 of the second section 25 is less than 2 mm, a surgical field of view of the user may be blocked by the support 10 having a certain diameter w2. Therefore, when the diameter w1 of the probe 20 is 70 μm, the length d2 of the second section 25 is advisably 2 mm or more and 6 mm or less.

Accordingly, when the diameter w1 of the probe 20 is 70 μm, the ratio of the diameter w1 of the probe 20 to the length d2 of the second section 25 of the probe 20 may be 0.0116 or more and 0.035 or less.

In this case, the diameter w1 of the probe 20 is smaller than the diameter of the conventional probe which is formed to be 120 μm, thereby securing a field of view of a user 5 (see FIG. 5) such as a doctor during surgery. In particular, the precision of surgery (e.g., ophthalmic surgery) performed in a relatively narrow area unlike other surgical surgeries may be improved.

Referring to FIGS. 1 and 2, the ratio of the diameter w1 of the probe 20 to the diameter w2 of the support 10 according to an embodiment of the present disclosure may be 0.03 or more and 0.07 or less. Specifically, when the diameter w2 of the support 10 is 1 mm, the diameter w1 of the probe 20 may be 30 μm or more and 70 μm or less.

In particular, when the diameter w2 of the support 10 is 1 mm, the diameter w2 of the support 10 is smaller, by 0.8 mm, than the diameter of the conventional support, which is 1.8 mm. Because the diameter (or thickness) of the support 10 is reduced, a field of view of a user such as a doctor may be secured during surgery, and in particular, the precision of surgery (e.g., ophthalmic surgery) performed in a relatively narrow area unlike other surgical surgeries may be improved.

Referring to FIGS. 1, 2 and 4, the probe 20 according to an embodiment of the present disclosure may be formed in a straight shape. Because the probe 20 is formed in a straight shape, the user may accurately bring the probe 20 into contact with a damaged portion.

Referring to FIG. 1, the first section 21 of the probe 20 is concentric with the support 10 formed in a cylindrical shape, and is inserted into the support 10. The probe 20, specifically, the first section 21, and the support 10 are both formed of a conductive material, and may be supplied with power through an electrical path, such as the electric wire C, arranged inside the handpiece body 50. The first section 21 and the second section 25 may be integrally formed of the same material.

The support 10 is inserted into the holder 40 according to an embodiment of the present disclosure. The holder 40 is coupled to the handpiece body 50 to be described later. The holder 40 may be reduced in diameter further away from the handpiece body 50.

Because the diameter of the holder 40 on the other side opposite to one side of the holder 40 coupled to the handpiece body 50 is reduced, a field of view at the probe 20, specifically, the second section 25, may be secured, and when the user brings the second section 25 into contact with the conjunctiva or the like, a field of view with respect to the probe 20 may be secured.

In the present disclosure, the cross section of the holder 40 may be formed in a circular shape based on an axis orthogonal to a longitudinal axis $X_1$ of the holder 40. However, the present disclosure is not limited thereto, and various modifications may be made. For example, a cross section of the holder 40 may be formed in a polygonal shape such as a triangle or a square, based on the axis orthogonal to the longitudinal axis $X_1$ of the holder 40.

Referring to FIGS. 1 and 2, the handpiece body 50 and the holder 40 are concentric with each other as a pencil, and may be arranged on the same straight line and coupled to each other. The holder 40 may be provided with openings on both sides thereof and coupled to the handpiece body 50 through an opening on one side. The support 10 may be inserted into the insertion portion 42 that is an opening on the other side opposite thereto, and the second section 25 of the probe 20 may protrude to the outside of the support 10.

The holder 40 may be provided with the insertion portion 42 such that the support 10 may be inserted into the insertion portion 42. The insertion portion 42 has a hollow interior, and the support 10 is inserted into the hollow interior. Referring to FIG. 1, the inner circumferential surface of the insertion portion 42 is formed to correspond to the shape of the outer circumferential surface of the support 10.

Specifically, the support 10 according to an embodiment of the present disclosure may be formed in a cylindrical shape, and the inner circumferential surface of the insertion portion 42 may be concentric along the longitudinal axis X1 of the insertion portion 42 so as to correspond to the shape of the outer circumferential surface of the support 10 and may be formed in a hollow cylindrical shape.

Referring to FIGS. 3 to 5, a longitudinal axis X2 of the handpiece body 50 and the longitudinal axis $X_1$ of the holder 40 may be arranged to form a certain angle θ. The longitudinal axis $X_1$ of the holder 40 is the same as the longitudinal axis of the support 10 inserted into and coupled to the holder 40 and the longitudinal axis of the probe 20 coupled to the support 20.

One end of the holder 40 may be coupled to one end of the handpiece body 50 facing the holder 40, and may be coupled to an edge along the outer circumferential surface of one end of the handpiece body 50. The holder 40 may be rotatably coupled to the handpiece body 50.

Because the holder 40 is rotatable at one end of the handpiece body 50, an angle θ formed by the longitudinal axis $X_2$ of the handpiece body 50 and the longitudinal axis $X_1$ of the holder 40, specifically, the holder body 41 may be adjusted.

Referring to FIGS. 3 to 5, the holder 40 according to an embodiment of the present disclosure includes a holder body 41, a button portion 43, and an elastic support 45. The holder body 41, into which the support 10 is inserted, is formed in a cylindrical shape to correspond to the shape of the support 10.

The support 10 is inserted into the holder body 41 through an opening formed on one side of the holder body 41, and when the use of the support 10 is completed, the support 10 is removed to the outside of the holder body 41 through the insertion portion 42 and is replaceable with a new support.

The holder body 41 may be reduced in diameter further away from the handpiece body 50. FIG. 4 is a cross-sectional view illustrating a cross section of the holder body 41, and as shown in FIG. 4, the holder body 41 may be reduced in diameter further away from the handpiece body 50. Although FIG. 4 illustrates a case where a change in the diameter of each section of the holder body 41 is linear, the present disclosure is not limited thereto. For example, a change in the diameter of each section of the holder body 41 may be non-linear and curved.

In the case where a change in the diameter of the holder body 41 is non-linear and curved, a reduction of the diameter of the holder body 41 may be greater than that of the handpiece body 50 towards the surgical site. Accordingly, when the user brings the probe 20 coupled to the support 10 into contact with a surgical target site while the user is holding the handpiece body 50, the field of view may be prevented from being blocked by the outer circumferential surface of the holder body 41.

Referring to FIGS. 3 to 5, the button portion 43 according to an embodiment of the present disclosure may be arranged on the other side opposite to one side of the holder body 41 where the insertion portion 42 is formed. The button portion 43 may be formed to allow reciprocating movement inside the holder body 41.

The elastic support 45 to be described later may be coupled to the button portion 43, and when the support 10 is inserted into the holder body 41 through the insertion portion 42, the support 10 presses the elastic support 45 and accordingly the button portion 43 may be moved to the rear (the left side in FIG. 4). The button portion 43 may be formed in a cylindrical shape.

The button portion 43 may have a stepped portion (not shown) along the outer circumferential surface thereof, and thus, even if the support 10 inserted into the holder body 41 through the insertion portion 42 presses the elastic support 45 and the button portion 43 coupled to the elastic support 45, the button portion 43 may be prevented from being released from the holder body 41.

Referring to FIGS. 3 to 5, the elastic support 45 according to an embodiment of the present disclosure may be arranged between the button portion 43 and the support 10 inserted into the inside of the holder body 41, and one end of the support 45 may be coupled to the button portion 43 and fixed in position. The elastic support 45 may be formed of a coil-shaped spring.

Hereinafter, the operation principle and effect of the ophthalmic surgical apparatus 1 according to an embodiment of the present disclosure are described.

Referring back to FIG. 1, the ophthalmic surgical apparatus 1 includes the support 10, the probe 20, the holder 40, and the handpiece body 50, as described above. The support 10 is provided with an electrical path, and power supplied from the outside is transmitted to the support 10 and the probe 20 coupled to the support 10, through a wire C arranged inside the handpiece body 50.

An RF signal is used in the ophthalmic surgical apparatus 1 according to the embodiment of the present disclosure, and the RF signal is transmitted to the handpiece body 50, the support 10, and the probe 20 coupled to the support 10, through electrical paths such as the wire C. The RF signal transmitted to the probe 20 is transmitted to a damaged portion such as the conjunctiva of the subject, in ophthalmic surgery.

The probe 20 may be formed of a conductive material, the first section 21 may be coupled to the support 10, that is, inserted into the support 10, the second section 25 may be integrally formed with and connected to the first section 21, and the entire surface of the second section 25 may be exposed to the outside of the support 10.

The first section 21 and the second section 25 may be formed of a conductive material and may be integrally connected to each other, and the first section 21 corresponding to a certain section of the probe 20 is inserted into the support 10.

Due to this, compared to a case where the probe 20 is directly coupled to the outer circumferential surface of the support 10, there is an effect that resistance to the shape deformation of the probe 20 increases.

Therefore, there is an effect of preventing the shape deformation of the probe 20 having a linear shape and securing rigidity against the shape deformation.

Because the entire surface of the probe 20, specifically, the second section 25 is exposed to the outside of the support 10, the outer circumferential surface of the second section 25 does not need to be surrounded by an insulating portion formed of an insulating material such as Teflon, and thus, a separate insulating portion is not required. Therefore, compared to a case where an insulating portion is coupled to the probe 20, there is an effect that the diameter of the probe 20 is reduced and the user's field of view is secured during surgery.

According to an embodiment of the present disclosure, the ratio of the diameter w1 of the probe 20 to the length d2 of the second section 25 of the probe 20 may be 0.0116 or more and 0.035 or less.

Due to this, when the ratio is less than 0.0116, that is, when the diameter w1 of the probe 20 is 70 μm, the rigidity of the second section may be secured compared to a case where the length d2 of the second section 25 exceeds 6 mm. In addition, as the length d2 of the second section 25 increases, the shape of the second section 25 may be prevented from being changed.

When the ratio of the diameter w1 of the probe 20 to the length d2 of the second section 25 is greater than 0.035, that is, when the diameter w1 of the probe 20 is 70 μm, the second section 25 may prevent the field of view from being obstructed by the support 10 or the like. In addition, when the user brings one end of the probe 20, specifically, one end of the second section 25, into contact with a surgical site, such as the conjunctiva, the support 10 coupled to the second section 25 may be prevented from interfering with a treatment portion such as the conjunctiva.

The support 10 and the probe 20 are concentrically coupled to each other. Specifically, the first section 21 corresponding to a certain section of the probe 20 is coupled to the support 10 and is arranged inside the support 10, and the second section 25 is connected to the first section 21 and is arranged outside the support 10.

In particular, because the entire surface of the second section 25 is exposed outside the support 10 and a separate insulating portion is not required, the thickness of the probe 20 may be prevented from being increased by the thickness of the insulating portion, and a field of view of the probe 20, specifically, the second section 25 may be secured.

Referring to FIGS. 1 and 2, the ratio of the diameter w1 of the probe 20 to the diameter w2 of the support 10, according to an embodiment of the present disclosure, may be 0.03 or more and 0.07 or less, and when the diameter w2 of the support 10 is 1 mm, the diameter w1 of the probe 20 may be 30 μm or more and 70 μm or less.

Because the ratio of the diameter w1 of the probe 20 to the diameter w2 of the support 10 is 0.03 or more and 0.07 or less, it is possible to prevent the user's field of view from being obstructed due to the diameter w2 of the support 10 in ophthalmic surgery, which is performed at a local site compared to other surgical surgeries, compared to a case where the ratio is less than 0.03, that is, the diameter w2 of the support 10 is less than 30 μm.

Compared to a case where the ratio of the diameter w1 of the probe 20 to the diameter w2 of the support 10 exceeds 0.07, that is, a case where the diameter w1 of the probe 20 exceeds 70 μm, the rigidity of the support 10 surrounding the first section 21 and coupled thereto may be secured.

As described above, the holder 40 according to an embodiment of the present disclosure includes the holder body 41, the button portion 43, and the elastic support 45. The holder body 41 is coupled to the handpiece body 50, and as shown in FIG. 1, the holder body 41 and the handpiece body 50 may share a longitudinal axis and be formed in a pen type. As shown in FIG. 3, the longitudinal axis of the handpiece body 50 and the longitudinal axis of the holder 40 may form a certain angle θ.

Referring to FIG. 3, the support 10 and the probe 20 coupled to the support 10 are coupled together through the insertion portion 42 formed in the holder body 41. As the support 10 is inserted into the inside of the holder body 41, the other end opposite to one end of the support 10 to which the probe 20 is coupled is in contact with the elastic support 45 arranged on a moving path of the support 10 in the inside of the holder body 41.

As the support 10 is moved from the inside of the holder body 41 to a certain position, the support 10 presses the elastic support 45 and thus the elastic support 45 is compressed. In the elastic support 45, an elastic restoring force is generated in a direction opposite to the insertion direction of the support 10, and the other side opposite to one side of the elastic support 45 in contact with the support 10 presses the button portion 43.

The button portion 43 is arranged on the other side (the left side in FIG. 4) opposite to one side (the right side in FIG. 4) of the holder body 41 in which the insertion portion 42 is formed, and the button portion 43 is moved to the left side (in FIG. 4) as the elastic support 45 presses the button portion 43.

When an ophthalmic surgery is completed, the user presses the button portion 43 in a direction (the right side in FIG. 5) opposite to a direction (the left side in FIG. 5) in which the button portion 43 protrudes from the holder body 41, and thus, the button portion 43 presses the elastic support 45 again. In this case, the elastic support 45 that is pressed may have an elastic restoring force in a direction (the right side in FIG. 5) away from the button portion 43 and may cause the support 10 inserted into the holder body 41 to be released to the outside of the holder body 41.

Accordingly, the user may remove a used support 10 and a used probe 20 coupled to the used support 10 from the holder 40, specifically, the holder body 41 by a simple operation of pressing the button portion 43, and may replace the used support 10 and the used probe 20 with a new support and a new probe.

The button portion 43 according to an embodiment of the present disclosure is movable from the inside of the holder body 41 in the same direction as an insertion or removal direction of the support 10.

Figure 6:
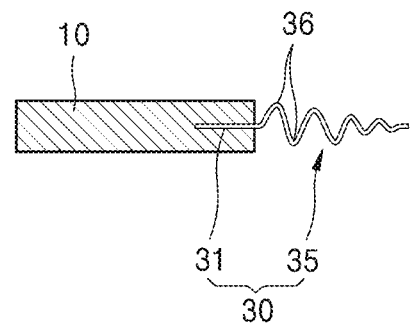
FIG. 6 is a side view illustrating a probe according to another embodiment of the present disclosure.

Hereinafter, the configuration, operation principle, and effects of an ophthalmic surgical apparatus according to another embodiment of the present disclosure will be described. FIG. 6 is a side view illustrating a probe 30 according to another embodiment of the present disclosure. The probe 30 may include a first section 31 and a second section 35, which are formed of a conductive material, and the first section 31 is inserted into and coupled to a support 10.

The second section 35 is integrally formed with and connected to the first section 31, and the probe 30, specifically, the second section 35, may have at least one bent portion 36 in a longitudinal direction. The bent portion 36 may have a curved shape, and thus, compared to the conventional probe having a longitudinal cross-section formed in a triangular shape, a contact area with a surgical site during the treatment of a tear duct may be reduced and thus the pain of the subject may be reduced, and a recovery time of a damaged portion may be shortened due to a reduction in the contact area with the surgical site.

The configuration of an ophthalmic surgical apparatus (not shown) including the probe 30 according to the other embodiment of the present disclosure is the same as that of the ophthalmic surgical apparatus 1 described above, except that the shape of the probe 30, specifically, the shape of the second section 35 is different from the shape of the probe 20, specifically, the shape of the second section 25. In detail, the support 10, the holder 40, and the handpiece body 50 in the ophthalmic surgical apparatus 1 described above are the same as those in the ophthalmic surgical apparatus (not shown) including the probe 30 according to the other embodiment of the present disclosure, and thus, repeated descriptions will be omitted.

Figure 7:
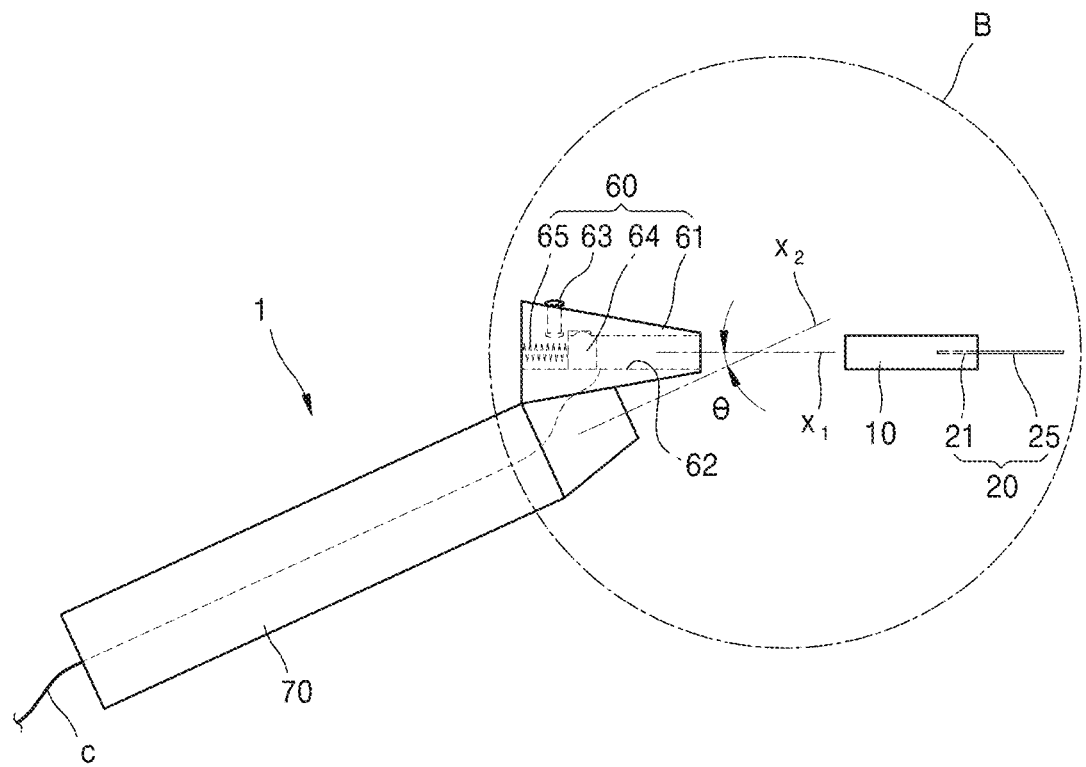
FIG. 7 is a side view illustrating an ophthalmic surgical apparatus according to another embodiment of the present disclosure.
Figure 8:
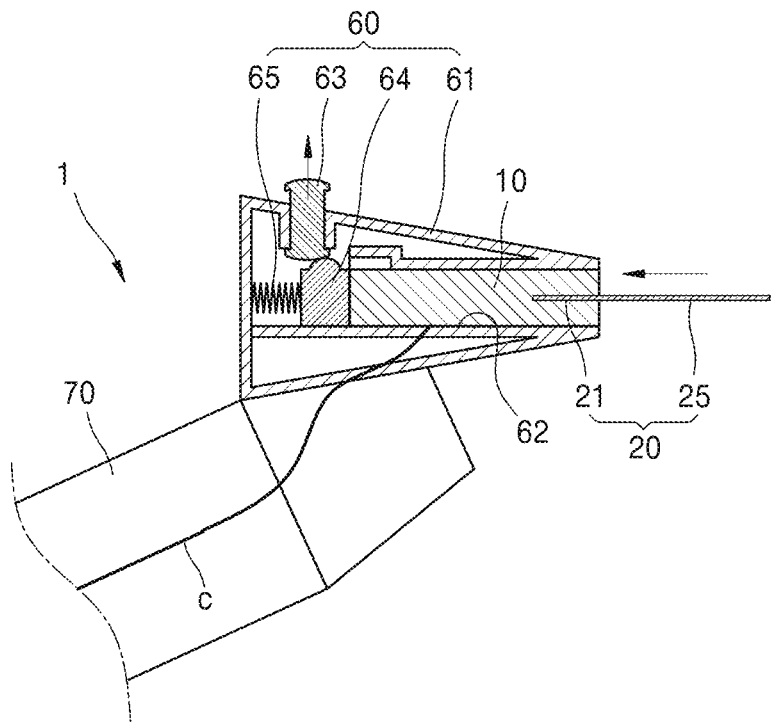
FIG. 8 is an enlarged view of portion B in FIG. 7.
Figure 9:
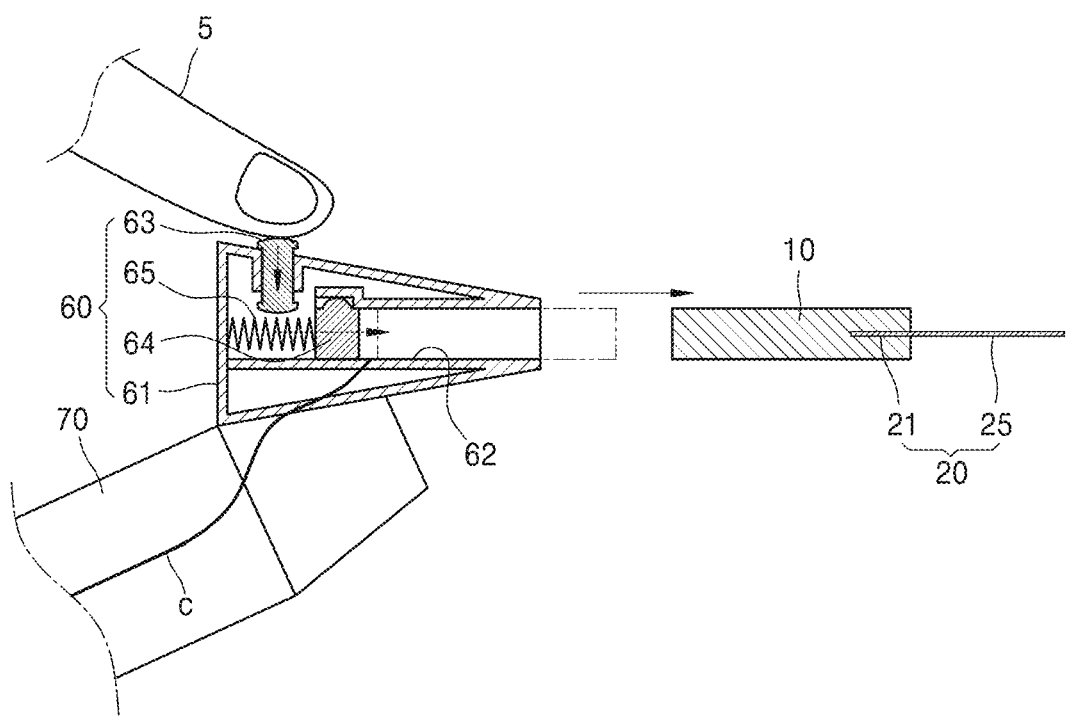
FIG. 9 is a side view illustrating a state in which a probe is removed from FIG. 7.

Hereinafter, the configuration, operation principle, and effects of an ophthalmic surgical apparatus according to another embodiment of the present disclosure will be described. FIG. 7 is a side view illustrating an ophthalmic surgical apparatus 1 according to another embodiment of the present disclosure. FIG. 8 is an enlarged view of a portion B in FIG. 7. FIG. 9 is a side view illustrating a state in which a probe is removed from FIG. 7.

The ophthalmic surgical apparatus 1 according to another other embodiment of the present disclosure may include a support 10, a probe 20, a holder 60, and a handpiece body 70. Referring to FIGS. 7 to 9, the holder 60 according to another embodiment of the present disclosure may include a holder body 61, a button portion 63, a moving portion 64, and an elastic support 65.

Referring to FIGS. 7 to 9, the holder body 61 is provided with an insertion portion 62 such that the support 10 is inserted therein. The insertion portion 62 may be formed to correspond to the shape of the outer circumferential surface of the support 10, and may be formed in a hollow cylindrical shape to correspond to the support 10 formed in a cylindrical shape.

The button portion 63 is penetratingly coupled to the holder body 61. A portion of the button portion 63 protrudes to the outside of the holder body 61, and the remaining portion of the button portion 63 except for the portion protruding to the outside of the holder body 61 is penetratingly coupled to the inside of the holder body 61.

The button portion 63 is provided with a stepped portion (not shown) protruding along the outer circumferential surface thereof, thereby preventing the button portion 63 from protruding beyond a certain portion to the outside of the holder body 61.

Referring to FIGS. 7 to 9, the moving portion 64 may be in contact with the button portion 63 and is formed to be movable on the insertion portion 62. The moving portion 64 is arranged on a moving path of the button portion 63.

One surface of the moving portion 64, which faces the button portion 63, may be formed in a curved shape, and thus, a contact area with the button portion 63 may be reduced and the button portion 63 may be prevented from being damaged due to friction between the button portion 63 and the moving portion 64.

Referring to FIGS. 7 to 9, the elastic support 65 is arranged between the holder body 61 and the moving portion 64, and elastically supports the moving portion 64 toward the support 10. One surface of the moving portion 64, which faces the button portion 63, protrudes toward the button portion 63, that is, is convex toward the button portion 63.

Referring to FIG. 8, the support 10 is inserted into the holder body 61 through the insertion portion 62 of the holder body 61, and the support 10 arranged inside the holder body 61 and the moving portion 64 contact each other.

Referring to FIG. 9, when the use of the support 10 and the probe 20 coupled to the support 10 is completed, the user presses the button portion 63 toward the moving portion 64 (the lower side in FIG. 9) to move the moving portion 64 toward the support 10 (the right side in FIG. 9).

In this case, as the button portion 63 presses the moving portion 64, the elastic support 65 is stretched and thus has an elastic restoring force in a direction (from the right side to the left side in FIG. 9) opposite to a moving direction of the moving portion 64. Because the moving portion 64 is returned to an original position again, the button portion 63 moves to the outside (the upper side in FIG. 9) of the holder body 61 and protrudes outward.

When the use of the support 10 and the probe 20 coupled to the support 10 is completed, the user presses the button portion 63 and moves the button portion from the inside of the holder body 61 in a first direction (from the upper side to the lower side in FIG. 9), and removes the support 10 and the probe 20 in a direction orthogonal to the moving direction of the button portion 63.

Due to this, when a support 10 and a probe 20 coupled to the support, which are disposable, are used, the used support 10 and the used probe 20 may be quickly removed from the holder body 61.

The configuration of the ophthalmic surgical apparatus 1 according to the other embodiment of the present disclosure is the same as that of the ophthalmic surgical apparatus 1 according to the above-described embodiment of the present disclosure, except for the configuration of the holder 60 including the holder body 61, the button portion 63, the moving portion 64, and the elastic support 65, and thus, repeated descriptions are omitted.

The embodiments have been described above. It will be understood by those of ordinary skill in the art that various changes in form and details may be made therein without departing from the spirit and scope of the present disclosure as defined by the appended claims. The scope of the present disclosure is set forth in the appended claims rather than the foregoing description and should be interpreted as including all differences within the equivalent range thereto.

INDUSTRIAL APPLICABILITY

According to an embodiment of the present disclosure, an ophthalmic surgical apparatus is provided. In addition, embodiments of the present disclosure may be applied to an industrially used electrosurgical instrument or the like.

The invention claimed is:

1. An ophthalmic surgical apparatus comprising:
a support provided with an electrical path; and
a probe formed of a conductive material,
wherein the probe includes a first section coupled to the support and a second section formed integrally with the first section and connected to the first section,
an entire surface of the second section is exposed to an outside of the support,
wherein a ratio of a diameter of the probe to a length of the second section of the probe ranges from 0.0116 to 0.035.

2. The ophthalmic surgical apparatus of claim 1, wherein a ratio of the diameter of the probe to a diameter of the support ranges from 0.03 to 0.07.

3. The ophthalmic surgical apparatus of claim 1, wherein the diameter of the probe ranges from 30 μm to 70 μm.

4. The ophthalmic surgical apparatus of claim 3, wherein the probe has a linear shape.

5. The ophthalmic surgical apparatus of claim 1, wherein the probe has at least one bent portion formed in a longitudinal direction.

6. The ophthalmic surgical apparatus of claim 1, wherein the support has a cylindrical shape.

7. The ophthalmic surgical apparatus of claim 1, wherein the first section of the probe is concentric with the support and is inserted into the support.

8. The ophthalmic surgical apparatus of claim 1, further comprising:
a holder into which the support is inserted; and
a handpiece body coupled to the holder.

9. The ophthalmic surgical apparatus of claim 8, wherein the holder is reduced in diameter further away from the handpiece body.

10. The ophthalmic surgical apparatus of claim 8, wherein a longitudinal axis of the handpiece body and a longitudinal axis of the holder are arranged to form a certain angle.

11. The ophthalmic surgical apparatus of claim 10, wherein the holder includes:
a holder body having an insertion portion formed for the support to be inserted into the insertion portion;
a button portion arranged on an opposite side of the insertion portion of the holder body; and
an elastic support arranged between the button portion and the support inserted inside the holder body.

12. The ophthalmic surgical apparatus of claim 11, wherein the elastic support includes a coil-shaped spring.

13. The ophthalmic surgical apparatus of claim 11, wherein the button portion penetrates the holder body and is reciprocally moved inside the holder body.

14. The ophthalmic surgical apparatus of claim 10, wherein the holder includes:
a holder body having an insertion portion formed for insertion of the support into the insertion portion;
a button portion penetratingly coupled to the holder body;
a moving portion that is in contact with the button portion and is movable on the insertion portion; and
an elastic support arranged between the holder body and the moving portion, the elastic support elastically supporting the moving portion toward the holder body.

* * * * *

UNITED STATES PATENT AND TRADEMARK OFFICE
CERTIFICATE OF CORRECTION

| | | |
|---|---|---|
| PATENT NO. | : 11,998,485 B2 | Page 1 of 1 |
| APPLICATION NO. | : 16/964707 | |
| DATED | : June 4, 2024 | |
| INVENTOR(S) | : Tchah et al. | |

It is certified that error appears in the above-identified patent and that said Letters Patent is hereby corrected as shown below:

On the Title Page

Item (12) delete "Chah" and insert -- TCHAH et al. --

First Column, Item (72), Please delete "Hung Won Chah" and insert -- Hungwon TCHAH --

Signed and Sealed this
Twenty-fifth Day of February, 2025

Coke Morgan Stewart
*Acting Director of the United States Patent and Trademark Office*